(12) United States Patent
Gruber et al.

(10) Patent No.: US 6,231,632 B1
(45) Date of Patent: May 15, 2001

(54) UREA PROCESSING AGENT

(75) Inventors: Karen A. Gruber, Hamilton; Shireen A. Mamun, East Windsor, both of NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/318,230

(22) Filed: May 25, 1999

(51) Int. Cl.$^7$ ..................................................... C05C 9/00
(52) U.S. Cl. ..................................... 71/28; 516/77; 516/79
(58) Field of Search ................... 71/28; 516/77, 516/79

(56) References Cited

U.S. PATENT DOCUMENTS

| | | | |
|---|---|---|---|
| 3,186,828 | * 6/1965 | Baarson et al. | 71/28 |
| 3,234,004 | * 2/1966 | Smith et al. | 71/28 |
| 3,686,305 | 8/1972 | Otsuka et al. | 260/555 |
| 3,690,931 | * 9/1972 | Jasnosz, Jr. | 71/28 |
| 3,697,245 | * 10/1972 | Dilday | 71/28 |
| 4,301,299 | 11/1981 | Inoue et al. | 564/67 |
| 4,670,588 | 6/1987 | Zardi | 564/72 |
| 4,864,059 | 9/1989 | Fujii | 564/71 |
| 4,885,021 | 12/1989 | Elrod et al. | 71/28 |
| 4,988,377 | * 1/1991 | Manalastas et al. | 71/28 |
| 5,403,956 | 4/1995 | Pagani | 564/67 |
| 5,622,658 | 4/1997 | Lloyd et al. | 264/15 |
| 5,628,813 | 5/1997 | Chen et al. | 71/64.02 |
| 5,676,729 | 10/1997 | Elrod et al. | 71/28 |
| 5,767,313 | 6/1998 | Jonckers | 564/71 |
| 5,782,951 | 7/1998 | Aylen et al. | 71/28 |
| 5,837,651 | 11/1998 | Hill | 504/116 |

FOREIGN PATENT DOCUMENTS

| | | |
|---|---|---|
| 3013616 | 9/1980 | (DE) . |
| 0628527A1 | 7/1993 | (EP) . |
| 998588 | 8/1961 | (GB) . |
| 1109665 | 3/1965 | (GB) . |

OTHER PUBLICATIONS

International Search Report (No Date).

* cited by examiner

Primary Examiner—Wayne Langel
(74) Attorney, Agent, or Firm—Raymond F. Keller

(57) ABSTRACT

In one embodiment, the present invention relates to a particulate urea composition containing particulate urea; kaolin; and a dispersant, wherein the dispersant is at least one of ammonia based dispersants, sulfonate dispersants, carboxylic acid dispersants and polymeric dispersants. In another embodiment, the present invention relates to a method of making urea, involving the steps of contacting a urea process stream with a slurry comprising a liquid, kaolin, and a dispersant, wherein the dispersant is at least one of ammonia based dispersants, sulfonate dispersants, carboxylic acid dispersants and polymeric dispersants; and recovering urea.

20 Claims, No Drawings

UREA PROCESSING AGENT

TECHNICAL FIELD

This invention generally relates to a urea processing agent useful in making particulate urea compositions and fertilizer compositions, and methods of making the urea compositions and fertilizer compositions.

BACKGROUND OF THE INVENTION

Urea is a leading source of solid form nitrogen in the fertilizer industry. This is because there are a number of advantages associated with urea over other fertilizers such as ammonium nitrate. In particular, urea has a high plant nutrient analysis. Urea is classified as a nonhazardous material whereas other fertilizers such as ammonium nitrate, under certain conditions, may be an explosive compound. Finally, environmental concerns such as minimizing air pollution are mitigated by using urea compared to many other fertilizers.

However, there are drawbacks associated with using urea as a fertilizer. When particulate urea is in the form of granules or prills, urea is highly friable due to relatively low hardness of the particles and prone to caking (prone to agglomeration). High friability is undesirable because the prills or granules tend to break into smaller particles, and produce substantial amounts of dust during handling, transportation, and application. Since urea products are often used in bulk blend fertilizer products, it is desirable for the urea to possess a predetermined, uniform size of granules to avoid unwanted segregation of the component products. If the urea product breaks into smaller particles, unwanted segregation of the urea may occur. Moreover, it is desirable for the urea to possess high hardness since urea granular products may break down when introduced into modern, rotating turbine-fan type field distribution equipment commonly used today. The breakdown of urea granules results in uneven distribution of the fertilizer from such equipment. And dusting is another undesirable consequence of relative low hardness.

Another concern with urea products is caking or agglomeration. Urea products are frequently transported, sold and used in large volumes and are thus transported and stored in bulk form. Because of the tendency for urea to cake or agglomerate, storage and transportation is not feasible without additional processing considerations that significantly add to the costs of production and/or handling. Furthermore, any additional processing must not involve undesirable reactions with the urea or raw materials used to make urea.

Attempts have been made to address these concerns. For example, it is known to incorporate formaldehyde and/or lignosulfonates into either the urea synthesis stream or the anhydrous molten urea melt stream. However, the use of formaldehyde is disfavored because it presents serious health and safety considerations. And the use of lignosulfonates can discolor the urea product to an unaesthetic brownish hue, with the result that the product is not well accepted in the marketplace.

The addition of a gelling type channelized 2:1 clay such as attapulgite or sepiolite to the urea melt stream or the urea synthesis stream is also known. Urea made with attapulgite or sepiolite has certain undesirable characteristics including color and increased agglomeration. Environmentally friendly urea products having increased hardness and increased resistance to agglomeration are desired.

SUMMARY OF THE INVENTION

In one embodiment, the present invention relates to a particulate urea composition containing particulate urea; kaolin; and a dispersant, wherein the dispersant is at least one of ammonia based dispersants, sulfonate dispersants, carboxylic acid dispersants and polymeric dispersants.

In another embodiment, the present invention relates to a method of making urea, involving the steps of contacting a urea process stream with a slurry comprising a liquid, kaolin, and a dispersant, wherein the dispersant is at least one of ammonia based dispersants, sulfonate dispersants, carboxylic acid dispersants and polymeric dispersants; and recovering urea.

In yet another embodiment, the present invention relates to method of making fertilizer, involving combining a particulate urea composition comprising particulate urea, kaolin, and a dispersant, wherein the dispersant is at least one of ammonia based dispersants, sulfonate dispersants, carboxylic acid dispersants and polymeric dispersants, with a fertilizer material to provide a fertilizer.

The present invention relates to an improved urea particulate compositions useful for direct application to the soil, as an intermediate product for the subsequent incorporation with other fertilizer materials into solid bulk blends, or in any application facilitated by the use of high hardness and/or anti-caking urea particulate compositions. The urea particulate compositions of the present invention have improved anticaking and nonfriable characteristics which render it superior to urea fertilizer granules produced by incorporation of gelling type 2:1 clays into an urea synthesis liquor.

DETAILED DESCRIPTION OF THE INVENTION

The present invention relates to particulate urea compositions, methods of making urea, fertilizers containing or made from particulate urea compositions, and methods of making fertilizers. The particulate urea has improved hardness, nonfriable and anti-caking properties compared to particulate urea made using conventional techniques.

Any form of kaolin may be employed with the present invention. This includes unbeneficiated kaolin, beneficiated kaolin, hydrous kaolin, treated hydrous kaolin, heat treated kaolin, and treated calcined kaolin. Treated hydrous kaolin and treated calcined kaolin include particles that are treated with a chemical, such as siloxane or stearate, to modify the properties. For example, the hydrophobicity or hydrophilicity of the kaolin may be modified by chemical treatment. Examples of hydrous kaolins that are commercially available from Engelhard Corporation, Iselin, N.J. are the hydrous kaolins sold under the trademark ASP®.

Heat treatment in accordance with the invention involves heating kaolin at a temperature from about 300° C. to about 1,200° C. for about 10 seconds to about 24 hours. In a preferred embodiment, heat treatment involves heating kaolin at a temperature from about 400° C. to about 1,100° C. for about 1 minute to about 15 hours. In a more preferred embodiment, heat treatment involves heating kaolin at a temperature from about 500° C. to about 1,000° C. for about 10 minutes to about 10 hours. The heat treatment may be carried out in air, in an inert atmosphere or under a vacuum.

In one embodiment, kaolin contains from about 1% to about 99% by weight of heat treated kaolin and from about 1% to about 99% by weight of hydrous kaolin. In another embodiment, kaolin contains from about 5% to about 95% by weight of heat treated kaolin and from about 5% to about 95% by weight of hydrous kaolin. In yet another embodiment, kaolin contains from about 10% to about 90% by weight of heat treated kaolin and from about 10% to about 90% by weight of hydrous kaolin. In still yet another embodiment, kaolin contains from about 20% to about 80% by weight of heat treated kaolin and from about 20% to about 80% by weight of hydrous kaolin.

In one embodiment, the heat treated kaolin comprises calcined kaolin. Examples of heat treated kaolins that are commercially available from Engelhard Corporation, Iselin, N.J. are the calcined kaolins sold under the trademark Satintone® and the siloxane treated calcined kaolins sold under the trademark Translink®.

In one embodiment, kaolin is a particulate material having a median individual particle size below about 25 microns. In another embodiment, kaolin is a particulate material having a median individual particle size below about 10 microns. In yet another embodiment, kaolin is a particulate material having a median individual particle size below about 5 microns. In still yet another embodiment, kaolin is a particulate material having a median individual particle size below about 1 micron. Particle size and particle size distribution as used herein are measured with a Micromeritics Sedigraph 5100 Particle Size Analyzer. Measurements are recorded in deionized water for hydrophilic particles. Dispersions are prepared by weighing 4 grams of dry sample into a plastic beaker adding dispersant and diluting to the 80 ml mark with deionized water. The slurries are then stirred and set in an ultrasonic bath for 290 seconds. Typically, for hydrous kaolin 0.5% tetrasodium pyrophosphate is used as a dispersant. Typical densities for the kaolin product are programmed into the sedigraph, e.g., 2.58 g/ml for hydrous kaolin. The sample cells are filled with the slurries and the X-rays are recorded and converted to particle size distribution curves by the Stokes equation. The median particle size is determined at the 50% level.

In one embodiment, kaolin has a particle size distribution wherein at least about 90% by weight of the kaolin particles have a particle size of about 25 microns or less. In another embodiment, kaolin has a particle size distribution wherein at least about 90% by weight of the kaolin particles have a particle size of about 10 microns or less. In yet another embodiment, kaolin has a particle size distribution wherein at least about 90% by weight of the kaolin particles have a particle size of about 5 microns or less. In a preferred embodiment, kaolin has a particle size distribution wherein at least about 90% by weight of the kaolin particles have a particle size of about one micron or less. In this connection, kaolin used in the present invention has a relatively narrow particle size distribution.

Kaolin is inert and has low toxicity. As used herein, "inert" means that the kaolin particles do not react with components of the urea reaction stream or the urea hot melt stream. Kaolin has extremely low toxicity meaning that in the quantities needed for effective urea processing, kaolin is not considered harmful to the environment (including use in a fertilizer), persons involved in its use according to the invention and the ultimate consumer.

Kaolin is combined with a liquid to form a slurry. The liquid is typically water but may also include organic liquids and water-organic liquid mixtures. The slurry may also be prepared from a water-urea solution. The organic liquids that may be employed are organic solvents, preferably organic solvents that do not react or deleteriously effect any of the components in the urea processing stream. In one embodiment, the organic liquid is a low boiling organic liquid.

The low boiling organic liquids are preferably water-miscible and contain from 1 to about 6 carbon atoms. The term "low boiling" as used herein shall mean organic liquids which have a boiling point generally no more than about 100° C. These liquids contribute to the ability of kaolin to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is a preferred low boiling organic liquid.

The low boiling organic liquids are used in an amount sufficient to form a dispersion of kaolin. In one embodiment, the amount of low boiling organic liquid in an aqueous slurry is up to about 30 volume percent of the dispersion, preferably from about 1 up to about 20 volume percent, and most preferably from about 2 to about 10 volume percent. Kaolin is preferably added to a low boiling organic liquid to form a slurry and then this slurry is diluted with water to form an aqueous dispersion. The resulting slurry retains the particles in finely divided form wherein most of the particles are dispersed to a particle size of less than about 25 microns.

In one embodiment, the kaolin slurry contains from about 25% to about 75% by weight liquid and from about 25% to about 75% by weight kaolin. In another embodiment, the kaolin slurry contains from about 30% to about 70% by weight liquid and from about 30% to about 70% by weight kaolin. In another embodiment, the kaolin slurry contains from about 35% to about 65% by weight liquid and from about 35% to about 65% by weight kaolin.

The kaolin slurry contains an effective amount of at least one dispersant. The dispersant facilitates the dispersion of the kaolin, and particularly increases the solids loading of the slurry. The dispersants may be preformed and added to the slurry or formed within the slurry.

The slurry is typically neutral; that is, having a pH from about 6 to about 8, and preferably from about 6.5 to about 7.5. The pH of the slurry may be adjusted, if necessary, by the addition of an acid or base so that the final pH of the slurry is approximately neutral. Formation of the slurry is typically conducted at ambient temperature and at atmospheric pressure. Higher or lower temperatures and pressures may be used but are not necessary.

Dispersants suitable for use in the present invention include organic dispersants and inorganic dispersants. Dispersants generally include ammonia based dispersants, sulfonate dispersants, carboxylic acid dispersants and polymeric dispersants, such as polyacrylate dispersants. The dispersants do not react or deleteriously effect any of the components in the urea processing stream.

In one embodiment, the slurry contains from about 0.1% to about 25% by weight of the kaolin of one or more dispersants (either added to the slurry or formed within the slurry). In another embodiment, the slurry contains from about 0.2% to about 20% by weight of the kaolin of one or more dispersants. In yet another embodiment, the slurry contains from about 0.5% to about 15% by weight of the kaolin of one or more dispersants.

Sulfonate dispersants include naphthalene sulfonates, alkylnaphthalene sulfonates, ethoxylated alkylphenol sulfonates, petroleum sulfonates, fatty acid sulfonates, lignosulfonates, olefin sulfonates, amine sulfonates, and alkylaryl sulfonates. Specific examples-Pacific Chemical Division, those under the trade designation Morwet® available from Witco Corp., those under the trade designation Sellogen available from Henkel Corp., and those under the trade designation Emkapon available from Emkay Chemical Co.

Carboxylic acids include typically include organic acids and their corresponding salts containing from about 6 to about 25 carbon atoms. In another embodiment, carboxylic acids contain from about 8 to about 20 carbon atoms.

Polyacrylates include polyacrylic acid, salts of acrylic copolymers, acrylic acid copolymers (for example with maleic acid), ammonium, alkali metal and alkaline earth metal polyacrylates and polycarboxylate salts. Specific examples include those under the trade designations Acumer® and Acusol available from Rohm & Haas Co., those under the trade designation Nopcosperse available from Henkel, and those under the trade designation Colloid available from Rhone-Poulenc Corp.

Ammonia based dispersants include the ammonium polyacrylates and the ammonium polycarboxylate salts mentioned in the paragraph above as well as ammonium hydroxide dispersants.

In one embodiment, the kaolin slurry compositions also contain a minor amount (less than about 25% by weight) of a flocculating or suspending agent may also be incorporated into the mixture to facilitate dispersion/suspension of the kaolin particles in the liquid medium. In addition, materials other than kaolin may be incorporated into the mixture. For example, a minor amount of special water-soluble or water-dispersible sorbents (e.g., silicas, aluminas or other clays) to selectively adsorb phosphorus or other deleterious compounds. Additional additive materials include gypsum, alkali salts, hydrated kiln dust, hydrated lime, fly ash, plasticizing agents, etc.

In one embodiment, the kaolin slurry compositions do not contain a hygroscopic phosphate compound, such as a phosphate based dispersant. In some instances, hygroscopic phosphate compounds, especially phosphate based dispersants, tend to deleteriously increase the hygroscopic nature of the resultant urea products.

The kaolin slurry is contacted with a urea melt stream or a urea synthesis stream to provide the particulate urea composition according to the present invention. Collectively, a urea melt stream and a urea synthesis stream are referred to as a urea process stream. Methods of providing a urea melt stream or a urea synthesis stream are known. For example, U.S. Pat. Nos. 3,607,938; 3,666,807; 3,668,250; 3,686,305; 4,061,675; 4,115,449; 4,301,299; 4,504,679; 4,801,744; 4,801,746; 4,801,747; 4,864,059; 5,276,183; 5,403,956; 5,409,358; and 5,767,313 describe urea melt streams and/or urea synthesis streams, and these patents are incorporated by reference for their teachings in these regards.

Generally speaking, a urea synthesis stream includes contacting ammonia and carbon dioxide at elevated temperatures and pressures forming ammonium carbonate, which in turn forms urea via dehydration. In one embodiment, the kaolin slurry is contacted with the urea synthesis stream including ammonia and carbon dioxide. An aqueous solution of urea is formed, followed by concentration techniques to provide a particulate urea composition.

Generally speaking, a urea melt stream includes urea crystals that are obtained from an aqueous solution of urea via concentration techniques. The urea crystals are melted or concentrated directly into a melt stream using conventional techniques and the kaolin slurry is contacted with the urea melt stream to provide a particulate urea composition.

The particular method of providing a urea melt stream or a urea synthesis stream are not critical to the present invention. Mild agitation may be employed in some instances to facilitate a more uniform mixture of the kaolin slurry with either the urea melt stream or the urea synthesis stream.

Kaolin and the dispersant facilitate the formation of at least one of high hardness urea, nonfriable urea and anticaking urea. The amount of kaolin slurry contacted with a urea process stream in accordance with the present invention depends primarily upon the amount of kaolin in the kaolin slurry and the amount of the urea in the urea process stream. In one embodiment, the amount of kaolin slurry contacted with the urea process stream is sufficient to provide a concentration from about 0.01% to about 10% kaolin based on the mass of urea. In another embodiment, the amount of kaolin slurry contacted with the urea process stream is sufficient to provide a concentration from about 0.05% to about 5% kaolin based on the mass of urea. In yet another embodiment, the amount of kaolin slurry contacted with the urea process stream is sufficient to provide a concentration from about 0.1% to about 2% kaolin based on the mass of urea.

The kaolin slurry or the particulate urea composition may contain one or more inorganic materials. Inorganic materials include calcium oxide, calcium hydroxide, calcium bentonite, sodium bentonite, non-kaolin clays, zeolite, cement, diatomaceous earth, fly ash quartz, cristobalite and muscovite. Diatomaceous earth is often found in deposits mixed with substantial quantities of other minerals such as clay. Diatomaceous earth and/or non-kaolin clay, in addition to kaolin, may in some instances serve to further improve the hardness of urea granules.

In one embodiment, the particulate urea composition according to the invention contains from about 85% to about 99.99% by weight particulate urea; from about 0.01% to about 10% by weight kaolin; and from about 0.00001% to about 5% by weight of a dispersant. In another embodiment, the particulate urea composition according to the invention contains from about 90% to about 99.95% by weight particulate urea; from about 0.05% to about 5% by weight kaolin; and from about 0.0001% to about 1% by weight of a dispersant. In yet another embodiment, the particulate urea composition according to the invention contains from about 95% to about 99.9% by weight particulate urea; from about 0.1% to about 2% by weight kaolin; and from about 0.0005% to about 0.3% by weight of a dispersant.

The particulate urea compositions produced in accordance with the present invention can be formed or converted into any physical state such as powder, prills, granules, and pellets. Preferably, the particulate urea compositions are anhydrous. In this connection, the particulate urea compositions contain less than about 0.1% by weight water. In another embodiment, the particulate urea compositions contain less than about 0.01% by weight water.

Urea produced in accordance with the present invention can be used as a fertilizer, a component of a fertilizer, an animal feed (such as a feed supplement for ruminants), a raw material for the production of urea-formaldehyde resins, a raw material for plastics manufacture, and a reagent in pharmaceutical preparations. In embodiments where urea produced in accordance with the present invention is used as a fertilizer, it is applied directly to the soil where it functions as a nitrogen release fertilizer.

In embodiments where urea produced in accordance with the present invention is used as a component of a fertilizer, it is combined with a fertilizer material. Fertilizer materials include at least one of a phosphate compound, a calcium compound, a potassium compound, a magnesium compound, a sulfur compound and a nitrogen compound. Generally speaking, fertilizer materials include at least one of a phosphate salt, a calcium salt, a potassium salt, a magnesium salt, a sulfur salt and a nitrogen salt.

Phosphate compounds include acid phosphates, potassium phosphates, and ammonium phosphates. Calcium compounds include calcium cyanimide, calcium carbonate, and calcium sulfate. Potassium compounds include potash, potassium sulfate, potassium chloride, potassium nitrate, potassium phosphates, and nitrophophates. Magnesium compounds include magnesia, magnesium sulfate, and magnesium carbonate. Nitrogen compounds include urea not made in accordance with the present invention, ammonia, ammonium compounds such as ammonium nitrate, ammonium chloride, ammonium phosphates, and ammonium sulfate, sodium nitrate, potassium nitrate, and nitrophosphates. Sulfur compounds include sulfates such as ammonium sulfate, potassium sulfate, magnesium sulfate, and calcium sulfate.

In one embodiment where the particulate urea composition is a component of a fertilizer, the fertilizer contains from about 0.1% to about 99.9% by weight of a fertilizer material and from about 0.1% to about 99.9% by weight of the particulate urea composition, and optionally from about 0.1% to about 99.9% by weight of a filler. In another embodiment where the particulate urea composition is a component of a fertilizer, the fertilizer contains from about 1% to about 90% by weight of a fertilizer material and from about 1% to about 90% by weight of the particulate urea composition, and optionally from about 1% to about 90% by weight of a filler.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A particulate urea composition, comprising:

particulate urea;

kaolin; and a dispersant, wherein the dispersant is at least one member selected from the group consisting of ammonia based dispersants, carboxylic acid dispersants and polymeric dispersants.

2. A particulate urea composition according to claim 1, wherein the kaolin is hydrous kaolin.

3. A particulate urea composition according to claim 1, wherein the kaolin is calcined kaolin.

4. A particulate urea composition according to claim 1, wherein the kaolin comprises a particle size distribution wherein at least about 90% by weight of kaolin particles have a particle size of about 25 microns or less.

5. A particulate urea composition according to claim 1, with the proviso that the composition does not comprise a hygroscopic phosphate compound.

6. A particulate urea composition according to claim 1, comprising:

from about 85% to about 99.99% by weight particulate urea;

from about 0.01% to about 10% by weight kaolin; and from about 0.00001% to about 5% by weight of the dispersant.

7. A fertilizer composition comprising the particulate urea composition according to claim 1.

8. A method of making urea, comprising:

contacting a urea process stream with a slurry comprising a liquid, kaolin, and a dispersant, wherein the dispersant is at least one member selected from the group consisting of ammonia based dispersants, carboxylic acid dispersants and polymeric dispersants; and recovering urea.

9. A method of making urea according to claim 8, wherein the liquid comprises at least one member selected from the group consisting of water, low boiling organic liquids, and optionally urea.

10. A method of making urea according to claim 8, wherein the slurry comprises from about 25% to about 75% by weight of the liquid, from about 25% to about 75% by weight of kaolin, and from about 0.1% to about 25% by weight of the kaolin of the dispersant.

11. A method of making urea according to claim 8, wherein the slurry has a pH from about 6 to about 8.

12. A method of making urea according to claim 8, wherein the kaolin comprises from about 1% to about 99% by weight of hydrous kaolin and from about 1% to about 99% by weight of calcined kaolin.

13. A method of making urea according to claim 8, wherein the dispersant comprises at least one member selected from the group consisting of an ammonium polyacrylate dispersant and an ammonium hydroxide dispersant.

14. A method of making urea according to claim 8, wherein the kaolin comprises a particle size distribution wherein at least about 90% by weight of kaolin particles have a particle size of about 10 microns or less.

15. A urea composition prepared according to the method of claim 8.

16. A method of making fertilizer, comprising:

combining a particulate urea composition comprising particulate urea, kaolin, and a dispersant, wherein the dispersant is at least one member selected from the group consisting of ammonia based dispersants, carboxylic acid dispasants and polymeric dispersants, with a fertilizer material to provide a fertilizer.

17. A method of making fertilizer according to the method of claim 16, wherein the fertilizer material comprises at least one member selected from the group consisting of a phosphate compound, a calcium compound, a potassium compound, a magnesium compound, a sulfur compound and a nitrogen compound.

18. A fertilizer composition prepared according to the method of claim 16.

19. A particulate urea composition, comprising:

particulate urea;

kaolin; and an ammonium polyacrylate dispersant.

20. A particulate urea composition, comprising:

particulate urea;

kaolin; and an ammonium hydroxide dispersant.

* * * * *